(12) United States Patent
Clayson

(10) Patent No.: US 8,814,827 B2
(45) Date of Patent: Aug. 26, 2014

(54) RETRACTABLE SYRINGE

(76) Inventor: Simon Paul Clayson, Ellenbrook (AU)

( * ) Notice: Subject to any disclaimer, the term of this patent is extended or adjusted under 35 U.S.C. 154(b) by 950 days.

(21) Appl. No.: 12/447,857

(22) PCT Filed: Nov. 5, 2007

(86) PCT No.: PCT/AU2007/001700
§ 371 (c)(1),
(2), (4) Date: Apr. 29, 2009

(87) PCT Pub. No.: WO2008/055298
PCT Pub. Date: May 15, 2008

(65) Prior Publication Data
US 2011/0092914 A1    Apr. 21, 2011

(30) Foreign Application Priority Data

Nov. 6, 2006 (AU) .............................. 2006906164

(51) Int. Cl.
| | |
|---|---|
| *A61M 5/00* | (2006.01) |
| *A61M 5/32* | (2006.01) |
| *A61M 5/315* | (2006.01) |
| *A61M 5/50* | (2006.01) |
| *A61M 5/31* | (2006.01) |

(52) U.S. Cl.
CPC .............. *A61M 5/3234* (2013.01); *A61M 5/502* (2013.01); *A61M 5/31513* (2013.01); *A61M 5/3134* (2013.01); *A61M 5/508* (2013.01)
USPC ............................ 604/110; 604/194; 604/226

(58) Field of Classification Search
USPC .......... 604/181, 194, 195, 204, 221, 226, 229
See application file for complete search history.

(56) References Cited

U.S. PATENT DOCUMENTS 4,713,056 A * 12/1987 Butterfield .................... 604/110
4,921,486 A    5/1990 DeChellis et al.
(Continued)

FOREIGN PATENT DOCUMENTS

| CN | 2353392 Y | 12/1999 |
|---|---|---|
| CN | 1631460 A | 6/2005 |

(Continued)

OTHER PUBLICATIONS

Chinese Office Action for Chinese Application No. 200780041246.1 dated Jan. 10, 2011.

(Continued)

*Primary Examiner* — Nicholas Lucchesi
*Assistant Examiner* — Weng Lee
(74) *Attorney, Agent, or Firm* — Alston & Bird LLP

(57) ABSTRACT

A syringe including a barrel, a needle subassembly holder positioned in the barrel, and a needle subassembly positioned in the holder. The needle subassembly includes a needle hub releasably connected to the holder and a needle connected to the hub. Further, the syringe includes a piston slidably received by the barrel. The piston includes a piston body and a piston head having a releasable portion temporarily covering a hatchway. The piston also includes a valve positioned proximal of the hatchway and movable between blocking and passing positions. A user may push the piston distally beyond an injected position in which the piston head contacts the holder causing the holder to move distally and the hub to contact the barrel, causing the barrel to bow, thereby storing potential energy. When the potential energy reaches a threshold amount sufficient to overcome forces holding the hub in the holder, the barrel rebounds toward its un-bowed shape thereby propelling the needle hub and needle proximally past the releasable portion and the valve and into the piston body. The valve then automatically returns to the blocking position thereby ensuring that the needle subassembly does not move proximally out of the piston body.

24 Claims, 6 Drawing Sheets

(56) References Cited

U.S. PATENT DOCUMENTS

| | | |
|---|---|---|
| 5,578,011 A | 11/1996 | Shaw |
| 5,613,952 A * | 3/1997 | Pressly et al. ............ 604/110 |
| 5,632,733 A | 5/1997 | Shaw |
| 6,036,674 A | 3/2000 | Caizza et al. |
| 6,090,077 A | 7/2000 | Shaw |
| 6,203,529 B1 | 3/2001 | Gabriel et al. |
| 6,572,584 B1 | 6/2003 | Shaw et al. |
| 7,351,224 B1 | 4/2008 | Shaw |
| 2005/0070854 A1 | 3/2005 | Wright |
| 2005/0159705 A1* | 7/2005 | Crawford et al. ............ 604/110 |

FOREIGN PATENT DOCUMENTS

| | | | |
|---|---|---|---|
| EP | 1547634 A1 | 6/2005 | |
| WO | WO 96/40326 A1 | 12/1996 | |

OTHER PUBLICATIONS

International Search Report and Written Opinion of corresponding International Application No. PCT/AU2007/001700.

International Preliminary Report on Patentability of corresponding International Application No. PCT/AU2007/001700.

Chinese Office Action for Chinese Application No. 200780041246.1 dated Jul. 13, 2011.

Government of India Patent Office, First Examination Report for Application No. 759/MUMNP/2009, Jan. 16, 2014, 5 pages, India.

European Patent Office, Extended European Search Report for Application No. 07815504.1, Apr. 13, 2013, 4 pages, The Netherlands.

* cited by examiner

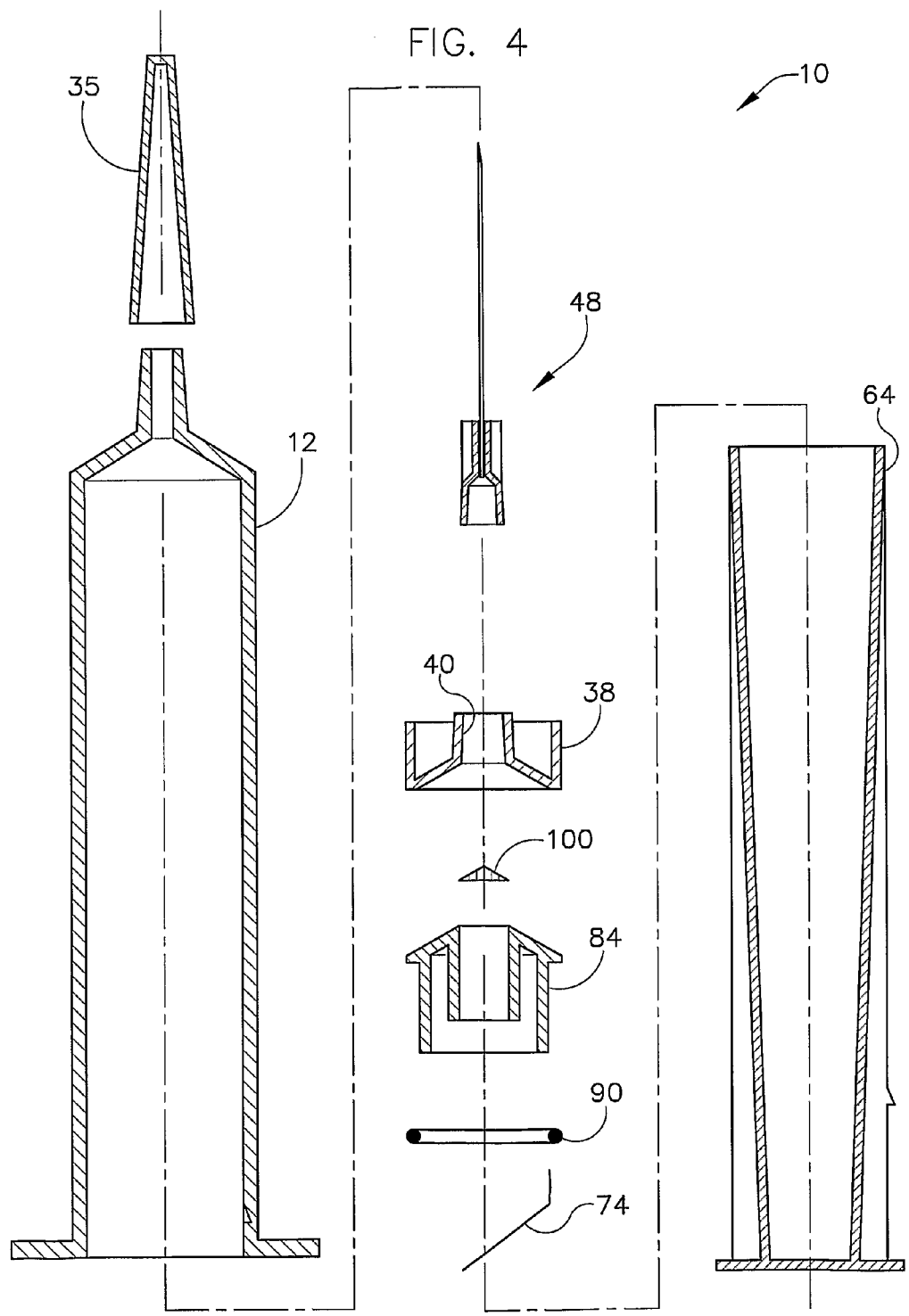

RETRACTABLE SYRINGE

FIELD OF THE INVENTION

Various embodiments of the present invention relate to a safety syringe assembly and, more specifically, to a safety syringe assembly having a retractable needle.

BACKGROUND OF THE DISCLOSURE

Distally extended needles of syringes that have been injected into patients pose risks of injury to medical personnel and of transmitting infectious diseases from accidental needle sticks during handling and disposal of the used syringes. Accidental needle sticks often occur because, for example, the syringe needles are usually relatively small, making them hard to see, and usually very sharp so that slight touches can pierce skin. Contaminated needles can carry blood-borne infectious agents, such as hepatitis B and C, human immunodeficiency virus (HIV), influenza, and tuberculosis, gonorrhea, and syphilis. Infected healthcare workers may transmit infections to patients, coworkers, family members, and others in the community. The Center for Disease Control has issued a recommendation that physicians and nurses avoid recapping used needles.

Various types of safety syringes allowing retraction of the needle from the dangerous extended distal position have been developed over recent years. These safety syringes have a variety of shortcomings including relatively low reliability and relatively high complexity, as well as relatively high manufacturing cost. Even a slight increase in manufacturing cost per syringe can be significant to manufactures and those in a distribution chain dealing with large amounts, perhaps millions, of the syringes per day.

Exemplary safety syringes include those having an internal spring system attached to a barrel of the syringe and to the needle for retracting the needle from its exposed distal position. These spring-loaded syringes are relatively complex and costly.

As another example, a safety syringe exists allowing a user to press a piston of the syringe against a hub connected to the needle and thereby engage the hub so the user can then pull the hub proximally, and thereby pull the needle from the exposed distal position. One problem with a syringe of this type is that it can only be used for a single injection because when the piston reaches a fully injected position, the piston engages the needle hub allowing withdrawal of the needle and the piston together, but disallowing subsequent relative motion between the piston and the needle, which would be required for additional fluid intake/expulsion.

BRIEF SUMMARY OF THE DISCLOSURE

Embodiments of the present invention relate to a retractable-needle syringe assembly including a hollow barrel extending from an open proximal end to an open distal end. The distal end defines a needle opening therein and the barrel has an inner surface and a proximally facing contact portion having at least one width. The syringe assembly further includes a needle subassembly holder positioned in the barrel adjacent the inner surface of the barrel and a needle subassembly. The needle subassembly includes a needle hub releasably connected to the holder, wherein the needle hub has a maximum width and a hub distal contact portion having a width being at least equal to the width of the barrel proximal contact portion. In some embodiments of the present invention, the needle hub includes a primary support connected to a secondary support by way of a luer fit. The syringe assembly also includes a needle connected to the needle hub and extending through the needle opening during a pre-retraction use of the syringe.

Further, the syringe assembly includes a piston subassembly slidably disposable within the barrel through the open proximal end of the barrel. The piston subassembly includes a piston body extending from a proximal end to a distal end and defining an inner region for receiving the needle subassembly during a retraction operation of the syringe assembly. The piston subassembly further includes a piston head positioned at or adjacent the distal end of the body. The piston head extends from a periphery to an edge of an inner hatchway and has a releasable portion temporarily covering an entirety of the hatchway and releasably connected to the edge of the hatchway. The hatchway has a width greater than the maximum width of the needle hub and the periphery of the head is configured to form a seal with the inner surface of the barrel when the piston subassembly is positioned within the barrel.

Embodiments of the present invention may also relate to a method of using a safety syringe assembly having a hollow barrel, a holder slidably disposed within the barrel, and a needle subassembly positioned in the barrel, releasably connected to the holder, and including a needle hub connected to a needle. The safety syringe used in the method may also include a piston subassembly slidably disposed within the barrel and having a hollow piston body and a piston head positioned adjacent a distal end of the body, the head extending from a periphery to an edge of a hatchway and having a releasable portion temporarily covering the hatchway and releasably connected to the edge. The needle subassembly may be positioned for pre-retraction use so that the needle extends through a distal opening of the barrel. The method includes providing the safety syringe with the piston head contacting the holder within the barrel and retracting the needle subassembly by pushing the piston subassembly distally within the barrel so as to apply, using the piston head, a distal force on the holder sufficient to move the holder distally. Moving the holder distally causes the needle hub held by the holder to press against a proximal contact portion of the barrel thereby causing the barrel to bow from an initial shape to store potential energy until the stored potential energy reaches a threshold value sufficient to cause the barrel to rebound toward the initial shape, thereby pushing the needle subassembly proximally to a safety position within the piston body.

BRIEF DESCRIPTION OF THE DRAWINGS

Having described various embodiments of the invention in general terms, reference will now be made to the accompanying drawings, which are not necessarily drawn to scale, and wherein:

FIG. 4 is an exploded cross section of the syringe shown in FIG. 1.

DETAILED DESCRIPTION OF THE DISCLOSURE

The present invention will now be described more fully hereinafter with reference to the accompanying figures, in which some, but not all embodiments of the invention are shown. Indeed, this invention may be embodied in many different forms and should not be construed as limited to the embodiments set forth herein. Rather, these embodiments are provided so that this disclosure will satisfy applicable legal requirements. Like numbers refer to like elements throughout.

The present invention includes embodiments of a syringe configured to allow retraction of a needle of the syringe from an exposed distal position. The needle may be retracted after the syringe has been used for expelling and/or taking in fluid. The syringe assembly includes a barrel and a needle subassembly, including a needle, releasably connected to the barrel so that the needle extends distally from the barrel. The needle subassembly may be releasably connected to a needle subassembly holder, which is in turn slidably received by the barrel. The syringe further includes a piston subassembly slidably received by the barrel and including a head having a hatchway and a releasable portion covering the hatchway.

The syringe is configured so that a user can selectively translate the piston subassembly distally and proximally with respect to the barrel for expelling/taking it fluids. The user may then retract the needle subassembly by first positioning the piston subassembly in a post injection position in which the head of the piston subassembly contacts the needle subassembly holder. The user then pushes the piston subassembly further in a distal direction thereby applying more force on the needle subassembly holder. The increased force on the holder causes the needle subassembly to press against the barrel, which, having elastic characteristics, bows in response, thereby storing energy.

When the potential energy being stored in the bowing barrel reaches a critical value sufficient to overcome forces (e.g., friction) holding the needle subassembly adjacent the needle subassembly hub, the potential energy transforms to kinetic as the bowed material rebounds back toward its original position thereby rapidly pushing the needle subassembly in a proximal direction, away from the exposed distal position. The propelled needle subassembly moves with force sufficient to dislocate at least some of the releasable portion of the head of the piston and pass through the hatchway and into a body of the piston. The syringe having its needle retracted from the exposed distal position in this way is safer for subsequent handling and disposal.

Figure 1:
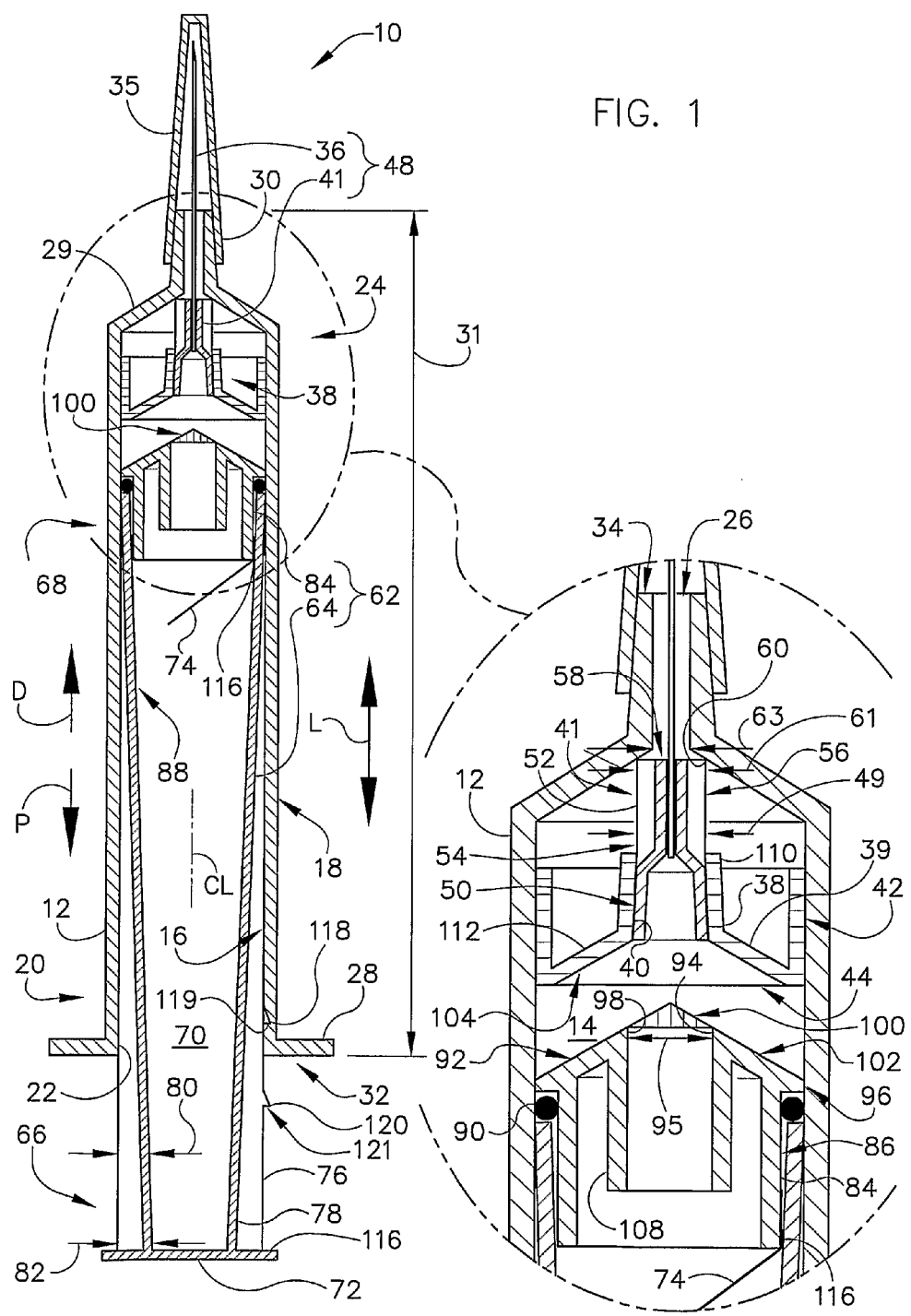
FIG. 1 is a side cross section of a syringe according to a first embodiment of the present invention.

Referring to the figures, and more particularly to FIG. 1, a syringe assembly according to a first embodiment of the present invention is designated in its entirety by reference number 10. The syringe assembly 10, or simply syringe, includes a hollow casing or barrel 12 forming an inner compartment 14 surrounded by an inner surface 16 and an outer surface 18 opposite the inner surface. The barrel 12 extends from a proximal end 20, including a proximal opening 22, to a distal end 24, including a distal opening 26.

The distal opening 26 has an engaging width 27, which is a diameter when the opening is generally circular. The distal opening 26 may have other widths greater and/or smaller than the engaging width 27 when the distal opening is not circular. The barrel 12 may also include one or more handling flanges 28 extending from the outer surface 14 of the barrel.

The barrel 12 may have various shapes and sizes without departing from the scope of the present invention. For example, as shown in FIG. 1, the distal end 24 of the barrel 12 may include a frustro-conical, or funneling or tapering, portion 29. The distal end 24 may also include a guiding nose portion 30 through which a needle 36 of the syringe 10 passes. The syringe 10 may also include a safety cap 35 for covering the needle 36 when the syringe is in the pre-retraction state and not being used to extract or inject fluid. The syringe 10 may be configured in a variety of ways so that the cap 35 releasably connects to the balance of the syringe 10 about the needle 36. For example, a distal part of the barrel 12, such as the guiding nose portion 30, may be configured for being snugly received by the cap 35, as shown in FIG. 1. As another example, the cap and a needle hub, to which the needle is directly connected, may be configured to releasably connect directly to each other, as described below regarding the embodiment exemplified in FIG. 6.

As another example of barrel 12 configurations, the barrel 12 may be generally cylindrical. For instance, the inner surface 16 may form a generally smooth cylinder, excepting contouring, such as the tapering portion 29 shown in FIG. 1. Similarly, the outer surface 18 may be generally cylindrical excluding that contouring and the flanges 28.

Although the barrel 12 may have other lengths 31 measured between a tip 32 of the proximal end 20 and a tip 34 of the distal end 24 without departing from the scope of the present invention, in one embodiment the barrel has a length between these tips of between about 70 mm and about 100 mm, such as between about 83 mm and 90 mm. The barrel 12 may have various inner widths 33 (i.e., an inner diameter when the barrel is generally cylindrical) measured between opposing points of the inner surface 16 across the inner compartment 14 of the barrel without departing from the scope of the present invention. For example, in one embodiment the barrel 12 has an inner width 33 of between about 10 mm and about 25 mm, such as being between about 15 mm and about 20 mm. Although the barrel 12 may include other materials without departing from the scope of the present invention, in many embodiments the barrel includes a common material used for syringe barrels, such as a relatively hard and lightweight plastic, which may be generally transparent or translucent.

The syringe 10 further includes a holder 38 positionable within the compartment 14 of the barrel 12. The holder 38 holds the needle 36 of the syringe 10 when the syringe is in an initial, pre-retraction, state in which the syringe is used to take in and expel fluid. The holder 38 includes a body 39 forming a cavity 40. The cavity 40 may be generally centrally located within the holder 38 and the syringe 10.

The syringe 10 further includes a needle base or hub 41 connected directly to the needle 36. As shown in FIG. 1, the needle hub 41 may directly hold the needle 36, and the holder 38 may directly, though temporarily, hold the needle hub and the needle, before the needle hub and the needle are retracted from their distal extended position shown in FIG. 1. The needle hub 41 may be sized and shaped in a variety of ways, and include a variety of materials, without departing from the scope of the present invention.

The holder 38 may be sized and shaped in a variety of ways, and include a variety of materials, without departing from the scope of the present invention. The holder 38 and the hub 41 may be configured so that the holder matingly receives the hub within the cavity 40. For example, the holder 28 and the hub 41 may be configured so that they can friction fit together. As shown in FIG. 1, the holder 38 may include an outer surface 42 that is sized and shaped to snugly engage the inner surface 16 of the barrel 12. In this and other embodiments, the holder 38 may be slidably received by and connected to the barrel 12 allowing the holder to slide with respect to the barrel when a sufficient or threshold force for overcoming a strength of the slidable connection between the holder 38 and the barrel is applied to the holder in the proximal or distal directions P, D. For example, for embodiments in which the holder 38 is only connected to the barrel 12 by a friction fit between the outer surface 42 of the holder and the inner surface 16 of the barrel, a sufficient force applied to a proximal end 44 of the holder in a distal direction D of the syringe 10 will overcome the friction force connecting the holder and barrel, thereby causing the holder to move distally with respect to the barrel.

The syringe 10 may be configured so that the relative motion between the holder 38 and the barrel 12 allows or causes relative motion between the needle base or hub 41 holding the needle 36 and at least some of the barrel. The role of the relative motion between the hub 41 and the barrel 12 is described below in further detail.

It is contemplated that the holder 38 may be connected to the barrel 12 in ways other than or in addition to the previously described friction fit, but still allowing relative motion between the holder and the barrel. For example, in one contemplated embodiment (not shown in detail), the holder 38 is connected to the barrel 12 by a temporary, breakable, connection. The breakable connection may include at least one weak and easily broken piece of material. The piece of material may be weak because, for example, the material is very thin. Accordingly, in this embodiment, application of a sufficient force to the proximal end 44 of the holder 38 will cause the holder to move distally with respect to the barrel 12 and therein break the temporary connection. As described in the preceding paragraph, such relative motion between the holder 38 and the barrel 12 can allow relative motion between the needle hub 41 holding the needle 36 and a portion of the barrel.

The needle 36 may be partially disposed within the needle hub 41. The needle 36 and the hub 41 may together be referred to as a needle subassembly 48. Accordingly, the holder 38, which temporarily holds the needle hub 41 of the needle subassembly 48, may be referred to as a needle subassembly holder. The needle hub 41 is releasably connected to the needle subassembly holder 38. In one embodiment, the needle hub 41 is positioned within the cavity 40 of the holder 38. The needle hub 41 may be releasably connected to the holder 38 in a variety of ways without departing from the scope of the present invention. For example, in some embodiments of the present invention, the needle hub 41 is friction-fit connected to the holder 38 as mentioned above.

Figure 2:
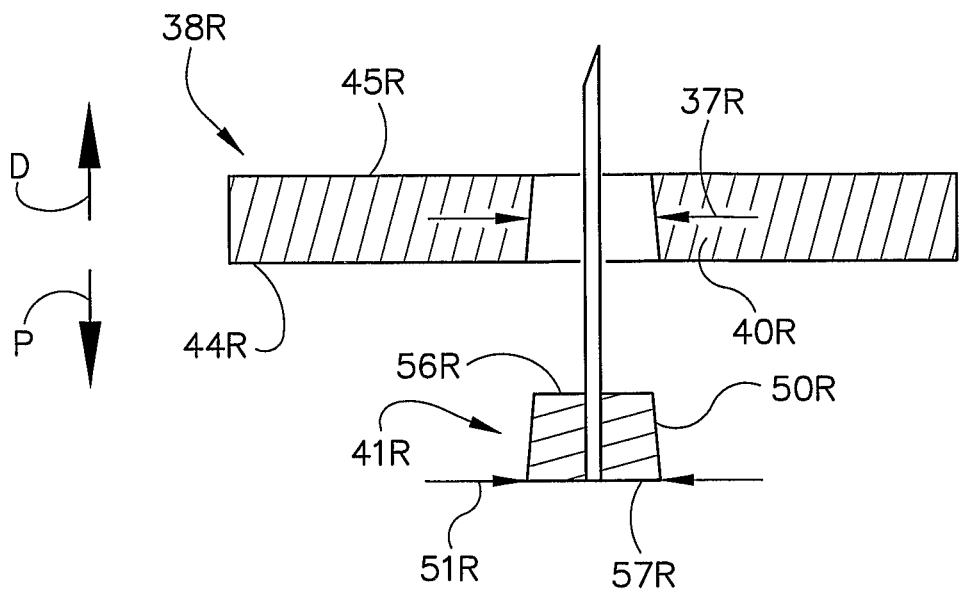
FIG. 2 shows a needle subassembly and a needle subassembly holder of a syringe having a reverse tapering arrangement.
Figure 3:
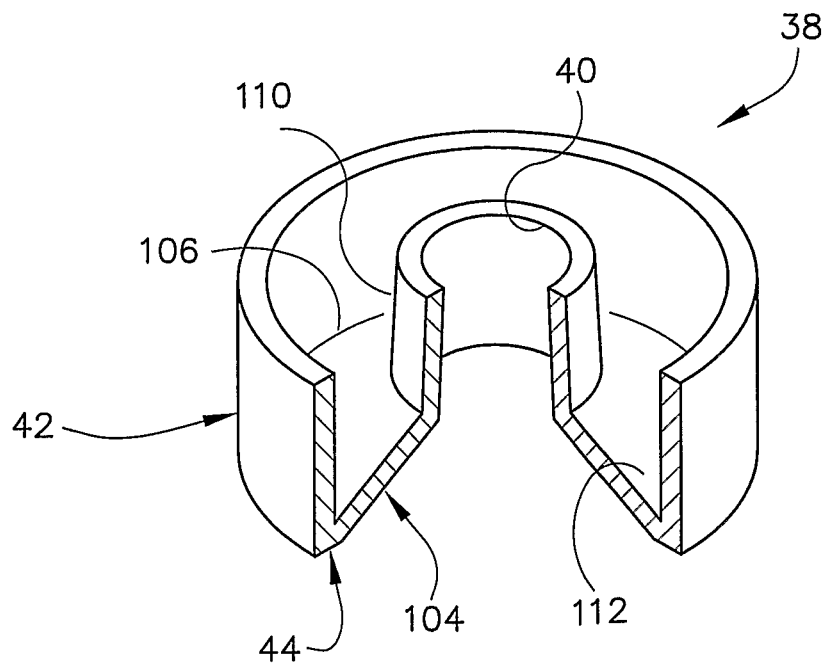
FIG. 3 is a perspective of a needle subassembly holder of the syringe shown in FIG. 1 shown with a portion of a front wall of the holder cut away.

The hub 41 and the holder 38 may have various shapes, such as corresponding taperings, for temporarily connecting to each other. In a conventional, so-called, normal tapering arrangement (not shown), a needle hub holding a needle is positioned on an outside distal nose of the barrel forming a snug fit between the hub and the barrel nose, which are thus held together by friction. On the contrary, the syringe 10 according to the present invention may include, as shown in FIGS. 2-4, a reverse taper fitting arrangement. In the reverse taper fitting arrangement, the inner cavity 40R of a holder 38R tapers from a larger width 37R adjacent a proximal end 44R of the holder or barrel distal end to a smaller width 37R adjacent a distal end 45R for receiving the outer surface 50R of the hub 41R, which likewise tapers from a larger width 51R adjacent a proximal end 57R of the hub to a smaller distal width at a distal end 56R of the hub. The holder 38R of this embodiment may be referred to as a reverse friction taper lock and the holder 38R may be referred to as a female taper fitting and the needle hub 41R may be referred to as a male taper fitting. As will be appreciated by those skilled in the art, the configuration of this embodiment, among other things, facilitates proximal propelling of the hub 41R with respect to the holder 38R due to the corresponding tapers. The needle hub 41R is mounted on the holder 38R in this reverse taper fitting arrangement by moving the hub distally into the holder 38R.

Further regarding the conventional, normal taper fit, arrangement (not shown), the barrel can be referred to as a male taper fitting, having an outer surface tapering from a large proximal size to a smaller distal size, and the needle hub may be referred to as a female taper fitting because its inner surface tapers from a larger proximal opening to a smaller distal opening for receiving the nose of the barrel. The needle hub is mounted on the barrel in this conventional normal taper fitting arrangement by moving the hub proximally onto the barrel nose.

In one contemplated embodiment (not shown in detail), the needle hub 41 is temporarily attached to the holder 38 by a breakable connection. The breakable connection between the needle hub 41 and the holder 38 may include at least one weak and easily broken piece of material, which may be weak because, for example, the material is very thin. It is also contemplated that the needle hub 41 and holder 38 may be releasably connected by both friction fit and breakable material. Further, regarding the needle hub 41 and the holder 28, the hub and the holder may be configured so that they can be friction fit together without having mating tapered surfaces. That is, the outer surface of the hub and the inner surface of the holder may be generally free of taper, but still sized and shaped to snugly mate by friction thereby creating the temporary fit needed to temporarily hold the hub and the holder together during use of the syringe before the retraction operation.

The needle hub 41 has a maximum width 49 and may include an outer surface 50 and one or more flanges 52 extending from the hub outer surface 50. For example, as shown in FIGS. 1 and 2, the needle hub 41 may include multiple flanges 52 extending longitudinally (i.e., proximally and distally) along the outer surface of the hub. For embodiments of the syringe 10 in which the needle hub 41 includes flanges 52, the maximum width 49 of the needle hub may be located between lateral tips 54 of opposing flanges 52 or between other parts of the hub besides the flanges, such as at a lower end (e.g., adjacent a proximal tip) of the hub.

The needle hub 41 has a distal end 56, which in some embodiments of the present invention has a contact portion 58. The barrel 12 of these embodiments has an internal contact portion 60 at or adjacent the distal end 24 of the barrel corresponding to the hub distal contact portion 58. The internal contact portion 60 of the barrel 12 may be referred to as a proximally facing portion 60 of the barrel 12. When the hub 41 is mounted on the holder 38, which is slidably positioned within the barrel 12, the hub, with the needle 36 and the holder, may be slid in a distal direction P of the syringe 10 until the contact portion 58 of the hub contacts the contact portion 60 of the barrel. As described above, the barrel 12 includes a distal opening 26. The needle 36 extends through this opening when the syringe 10 is in the pre-retraction state (e.g., FIGS. 1 and 5A-5C).

The hub distal contact portion 58 has a width 61 being at least equal to a width 63 of the corresponding contact portion 60 of the barrel 12 for, at least in part, ensuring that the contact portion 58 of the hub 41 engages the contact portion 60 of the barrel when the needle subassembly holder 38, the needle hub 41, and the needle 36 are slid in the distal direction D with the barrel.

The width 63 of the hub contact portion 58 may correspond to (e.g., be equal to) the maximum width 49 of the needle hub 41. The needle hub 41 contacting the barrel 12 may keep the needle hub from exiting the barrel and may allow the barrel to receive and store energy from the hub (e.g., by bowing in response to distal force exerted on the barrel by the hub) and then release that energy (e.g., reflect, rebound, or spring back to an original barrel shape) thereby propelling the needle in the proximal direction. More about this function and form of the barrel 12 related to this function are described below.

The syringe 10 further includes a plunger or piston subassembly 62 having a plunger or piston body 64 slidably received within the barrel 12, such as by way of the proximal opening 22 of the barrel. The piston body 64 extends between a proximal end 66 and a distal end 68 and defines a cavity or inner region 70. The piston body 64 may also include a cap 72, such as an end wall positioned adjacent the distal end 68 of the body. As described in more detail below regarding operation of the syringe 10, the piston body 64 receives the needle subassembly 48 when the syringe is self-destructed by the needle subassembly being retracted from the extended distal position (shown in FIG. 1). Moreover, for embodiments of the syringe 10 in which the piston body 64 includes the cap 72, the piston body can secure the needle subassembly 48 in the inner region 70 because the needle subassembly cannot pass out of the piston body in the distal direction due to the cap. Further, as described in more detail below, the piston body 64 may include a one-way valve 74 allowing the needle subassembly 48 to pass in the proximal direction P into the inner region 70 of the piston body 64 and impede the needle subassembly from passing in the distal direction D back out of the inner region of the piston body.

The piston body 64 may include longitudinal side flanges 76 extending partially or fully between the proximal end 66 and the distal end 68 of the body 64. As shown in FIG. 1, the piston side flanges 76 may extend from an outer surface 78 of the piston body 64 by a distance 80 varying between a maximum depth 82 adjacent the proximal end 66 of the piston body to zero depth adjacent the distal end 68 of the piston body. Primary purposes of the flanges 76 include strengthening the piston body 64 along a longitudinal direction L of the body. That is, the side flanges 76 can provide rigidity to the piston body 64 between the proximal and distal ends 66, 68 of the piston body, thereby enhancing an ability of the body to maintain its integrity as force is applied to the piston body in the distal and proximal directions D, P by a user for sliding the piston subassembly 62 with respect to the barrel 12 and against the needle hub 41.

Another purpose of the side flanges 76 is to reduce an amount of friction (i.e., coefficient of friction) between the piston body 64 and the barrel 12 when the piston body is slidably disposed within the barrel. Friction is reduced between the piston body 64 and the barrel 12 due to flanges 76 because the flanges contact less of the inner surface 16 of the barrel than would the outer surface 78 of the piston body if the piston subassembly where configured so that the outer surface 78 of the piston body defined an outer diameter being generally constant between the distal and proximal ends 68, 66 of the body (not shown). In the embodiment having a constant diameter outer surface 78 and lacking piston body side flanges, the outer surface of the piston body 64 would continuously contact the inner surface 16 of the barrel at all points of the piston outer surface positioned within the barrel 12 while the piston subassembly is being slid with respect to the barrel.

The piston subassembly 62 also includes a plunger or piston head 84 connected to the piston body 64 adjacent the distal end 68 of the piston body. It is contemplated that the piston body 64 and the piston head 84 may be unitary. That is, the piston body 64 and the piston head 84 may be found as a single piece. In other embodiments, as shown in FIG. 1, an outer surface 86 of the piston head 84 is connected to a corresponding inner surface 88 of the piston body 64. In other contemplated embodiments, an inner surface of the piston head 66 is connected to a corresponding outer surface of the piston body 64.

For embodiments of the present invention in which the piston head 84 is formed separate from and connected to the piston body 64, the head and the body may be connected in a variety of ways. For example, the head 84 and the body 64 may be sized and shaped so that one of the head or the body snugly fits within the other (i.e., of the body and the head) and is held in place by friction between the head and the body. As another exemplary type of connection, the piston head 84 and the piston body 64 may include corresponding connecting features, such as corresponding spiral grooves or notches (not shown), for being engaged together to hold the head in place adjacent the body.

The piston subassembly 62 may also include a sealing element 90 connected to the outer surface 78 of the piston body 64 or, as shown in FIG. 1, connected to the outer surface 86 of the piston head 84. An exemplary sealing element 90 is an o-ring, such as a conventional rubber o-ring. It is contemplated that the sealing element 90 may be unitary (i.e., formed as one piece) with the head 84, such as a flexible sealing flange (not shown) extending from the outer surface 86 of the piston head 84 to the inner surface 16 of the barrel 12.

The piston head 84 also includes a distal surface 92 defining a central aperture or hatchway 94. The hatchway 94 may have various shapes and sizes without departing from the scope of the present invention. For example, in one embodiment the hatchway 94 has a width 95 of between about 3 mm and about 7 mm, such as being between about 4 mm and about 6 mm. When the hatchway 94 is generally circular, the width 95 of the hatchway is a diameter. The width 95 of the hatchway 94 is about equal to or greater (e.g., slightly larger) than the maximum width 49 of the needle hub 41 so that the needle hub may pass through the hatchway, as described in further detail below.

The distal surface 92 extends from a periphery 96 adjacent the inner surface 16 of the barrel 12 to an edge 98 of the hatchway 94. The periphery 96 of the piston head 84 may be considered to include the sealing element 90 or be separate from the sealing element. The sealing element may be spaced longitudinally from more distal parts of the piston head 84, whether considered as part of the periphery or separate from the periphery.

The piston head 84 also includes a releasable portion 100 connected to the edge 98 of the hatchway 94 so that the releasable portion 100 sealingly covers the entire hatchway. Thus, the piston head 84, including the sealing element 90, the distal surface 92, and the releasable portion 100 are slidable within the barrel 12 and create a seal disallowing fluid disposed in the barrel 12 distal of the piston head from passing proximally beyond the piston head. The releasable portion 100 may be a generally circular disc having a small thickness and may be slightly conical. FIG. 4 shows an exploded view of the parts of the syringe 10. Although the releasable portion 100 is shown separated from the piston head 84 in FIG. 4 for simplicity of showing the various parts of the syringe 10, the releasable portion is connected to the piston head during use of the syringe before the retraction operation.

The releasable portion 100 is connected to the distal surface 92 of the piston head 84 by a temporary and breakable connection. The connection between the releasable portion 100 and the edge 98 of the distal surface 92 of the piston head 84 may include a relatively weak and easily broken or fractured piece of material, such as material being very thin and/or generally brittle. The connection may alternatively be a friction fit within the hatchway 94 wherein the releasable portion 100 and the distal surface 92 are sized and shaped so that the releasable portion can snuggly fit against the edge 98 of the hatchway to temporarily hold the releasable portion in place covering an entirety of the hatchway until a sufficient force moves the releasable portion.

The distal surface 92 of the piston head 84 or a portion of that surface form a distal contact area 102 and the needle subassembly holder 38 includes a corresponding or mating proximal contact area 104. When the piston subassembly 62 is positioned in the barrel 12 such as shown in FIG. 1, the piston subassembly 62 is slidable within the barrel so that at least some of the piston distal contact area 102 generally aligns with and contacts at least some of the proximal contact area 104 of the holder 38 when the piston subassembly is moved distally to the holder 38.

The piston distal contact area 102 and the holder proximal contact area 104 may have various shapes and sizes without departing from the scope of the present invention. For example, the distal contact area 102 of the piston head 84 may be generally convex, sloping from the periphery 96 distally and toward a centerline CL of the syringe 10 to the edge 98 of the hatchway, and the proximal contact area 104 of the holder 38 may be correspondingly generally concave, sloping from a periphery 106 of the holder distally and toward the centerline. The contact areas 102, 104 may be shaped and sized to ensure robust contact between the piston head 84 and the holder 38 so the piston 62 can push the holder effectively.

The piston head 84 may further include head structure 108 providing additional reinforcement to the head, such as at least one flange extending proximally from the edge 98 of the head surrounding the hatchway 94. The additional head reinforcing structure 108 in the embodiment shown in FIG. 1 includes a generally cylindrical flange extending proximally from the edge 98 of the piston head 84. A primary function of the additional reinforcing structure 108 is to provide additional strength to the piston head 84 and thereby to the entire piston subassembly 62 for ensuring that the head does not bend or fail in undesired ways while the head is being pushed against the holder and applies desired forces to the holder during operation of the syringe 10.

As shown in FIG. 3, the needle subassembly holder 38 may include a socket or holder structure 110 providing additional reinforcement to the holder. The additional holder structure 110 may extend distally from a holder base 112 of the holder wherein the base may include the proximal contact area 104 of the holder. The holder structure 110 may be considered part of the holder body 39 forming the cavity 40 of the holder. As shown in FIGS. 1 and 2, the holder base 112 base may taper, extending distally and inwardly from a periphery to a central portion adjacent the additional holder structure 110.

As shown in FIGS. 1 and 2, the additional holder structure 110 may include at least one flange extending distally from the base 112 of the holder. As also shown in FIG. 1, the additional holder structure 110 may be configured and positioned to form at least a part of the cavity 40 in which the needle hub 41 is initially positioned for use of the syringe 10.

The additional holder reinforcing structure 110 shown in FIG. 3 includes a generally cylindrical or frusto-conical flange extending distally from adjacent the cavity 40 of the holder. A primary function of the additional holder structure 110 is to provide additional strength to the holder 38 for ensuring that the holder does not bend or fail in undesired ways when the piston head 84 is pushing against the holder, yet allow the needle subassembly 48 to slip or break away from holder when sufficient energy is built up in the holder, the hub 41, and/or the barrel 12. It is contemplated that the holder 38 may be configured, such as by including the generally cylindrical or frusto-conical flange 110, so that energy can be built up in the holder and released to propel the needle subassembly away from the holder in combination with force built up in and from the hub 41 itself and/or the barrel 12 or alone. As described above regarding the reverse friction taper lock or reverse taper holder 38R, the hub 41R and the holder 38R configured generally as shown in FIG. 2 can also promote propelling the hub with respect to the holder, such as by contributing forces to the hub promoting propelling the hub, thereby decreasing an amount of energy required from other parts of the syringe to reach the threshold energy(s) needed to dislodge the hub from the holder.

As shown in FIG. 1 the barrel 12 and the piston body 64 may include conventional handling flanges 28, 114 extending generally laterally outward. The handling flanges 28, 114 are designed to be engaged by a user, such as by hands or a machine handling the syringe 10, for facilitating use of the syringe, including during use of the syringe for expelling and taking in fluid and for retracting the needle, as described in further detail below.

As described above, the piston subassembly 62 may include a one-way or check valve 74 adjacent and proximal of the piston head 84. The valve 74 may be configured to allow the needle subassembly 48 passing through the hatchway 94 in the proximal direction P to pass into the inner region 70 of the piston body 64 and disallow the needle subassembly from passing in the distal direction D back out of the inner region of the piston body (i.e., back through the hatchway).

Various types, sizes, and shapes of valves 74 may be used without departing from the scope of the present invention. For example, in one embodiment the valve 74 includes a flap of material biased toward a position in which it at least partially blocks a path between the inner region 70 of the piston body 64 and the hatchway 94. In this embodiment, the valve 74 is flexible for bending away from a biased or default (e.g., blocking) shape, state, or position when contacted by the needle subassembly 48 to a passing shape, state, or position, thereby allowing the needle subassembly to pass completely into the inner region 70 of the piston body 64 during the needle-retraction operation. After bending away from its biased shape and allowing the needle subassembly 48 to pass into the inner region 70 of the piston body 64, the valve 74 returns to a blocking shape, such as by automatically returning to the default biased shape, or near enough to the biased position to block a path between the needle subassembly 48 and the hatchway 94. Other one-way valves 74, including custom-made and conventional one-way valves 74 may be used for this purpose.

The valve 74 may include various materials without departing from the scope of the present invention. For example, in some embodiments the valve 74 includes a film or flap of paper, plastic, or another material that is relatively lightweight and inexpensive and yet effective for blocking the needle subassembly 48 as described above. The valve 74 may be generally soft so that it is relatively easily bendable (e.g., providing almost no resistance) from a blocking, closed, shape and an allowing, open, shape. The valve 74 is configured, such as by including a material having elastomeric characteristics, such that the valve 74 can automatically return to its blocking shape after being moved to its open shape by the needle subassembly 48. The syringe 10 may be configured such that primary purposes of the valve 74 include allowing the needle subassembly to easily pass proximally P past it and into the piston body 64 and to make it impossible for the needle 36 to point in, or perhaps even close to, the hatchway 94, thereby keeping the needle compartmentalized.

The valve 74 may be connected to the piston head 84 and the piston body 64 in a variety of ways, such as by being directly connected to the head and/or the body or indirectly connected to one or both of the head and body. For example, in embodiments of the syringe 10 in which the valve 74 includes a generally thin film or flap of material, as shown in FIG. 1, a base 116 of the valve may be disposed between the piston head 84 and the piston body 64 for securing the valve in place. Before, during, or after manufacture of the syringe 10 according to these embodiments, the valve 74 may be bent so that it turns from its base positioned between the piston head 84 and the piston body 64 so as to block the hatchway 94 sufficiently to keep the needle subassembly 48 form passing distally through the hatchway.

Alternatively, it is contemplated that the valve 74 may be integrally made (e.g., molded) with the piston head 84, the piston body 64, or both. That is the valve 74 may be formed as one piece with the piston head 84 and/or the piston body 64. The piston head 84 and the piston body may be integrally made.

In another aspect of the present invention, the barrel 12 and the piston subassembly 62 may be configured (e.g., sized, shaped, and including select materials) so that the piston subassembly is locked during or after the retraction operation from thereafter moving proximally with respect to the barrel. In this way, the piston subassembly 62 now containing the needle subassembly 48 may be kept securely in the barrel 12.

The locking configuration can take many forms being well within the designing ability of those skilled in the art. For example, it is contemplated that the barrel 12 and the piston subassembly 62 may include mating locking or connecting elements such as a female element 18 (e.g., notch or groove) on the barrel and a male element 120 (e.g., projection) on the piston body 64. Instead of the foregoing example, the barrel may include a male element corresponding to a female element of the piston, or the barrel and the piston may include mating male elements, such as two bumps or projections, which can engage each other during or after the retraction operation. The connecting element of the piston 62 may be positioned or formed in one of the piston flanges 76 or positioned on or formed in the piston body outer surface 78.

The connecting elements may be positioned at various locations of the piston subassembly 62 and the barrel 12, so long as they are matable (e.g., able to engage each other) during or after the retraction action. For example, as shown in FIGS. 1, 4, and 5A-5E, the connecting elements may be positioned adjacent proximal ends 20, 66 of the barrel 12 and the piston subassembly 62. As another example (not shown), the connecting elements may be positioned closer to the distal ends 24, 68 of the barrel 12 and the piston assembly 62. For instance, the connecting element of the piston subassembly 62 may be formed on or in the piston body 64 adjacent the distal end 68 of the piston body or be formed on or in the piston head 84 for engaging a corresponding connecting element formed on or in the distal end 24 of the barrel 12.

The connecting elements 118, 120 are configured to engage each other when the piston 62 is pushed past a fully injected position (see e.g., FIG. 5C) so that the piston can no longer move proximally with respect to the barrel. For example, as shown in FIG. 1, the piston body 62 may include a tapered male projection as the piston connecting element 120 having a proximal end 121 (e.g., flat proximal end) positioned adjacent the proximal end 66 of the piston and the barrel 12 may form a tapered female notch as the barrel connecting element 118 having a corresponding proximal end 119 (e.g., flat proximal end) adjacent its proximal end 20. When the user pushes the piston 62 distally beyond the injected position (e.g., FIG. 5C), the piston connecting element 120 engages the barrel connecting element 118 to lock the piston and barrel together. In one embodiment for locking, the piston connecting element 120 in the form of a projection will enter the barrel 12 when the piston subassembly 62 is moved distally with respect to the barrel. The barrel 12 may bend or bow to accommodate the projection. The piston connecting element 120 will then slide along the inner surface 16 of the barrel as the piston subassembly 62 is moved distally until the projection engages the barrel connecting element 118. For embodiments of the invention in which the barrel connecting element 118 is positioned close to a distal edge of the barrel 12, the connecting element 120 in the form of a projection may slide along the barrel inner surface 16 for a very short distance or not at all. The barrel 12 and/or the piston subassembly 62 may include a groove or channel (not shown in detail) for receiving a male connecting element of the other part until that male connecting element arrives as the corresponding connecting element, being male or female, for engagement.

Figure 5A:
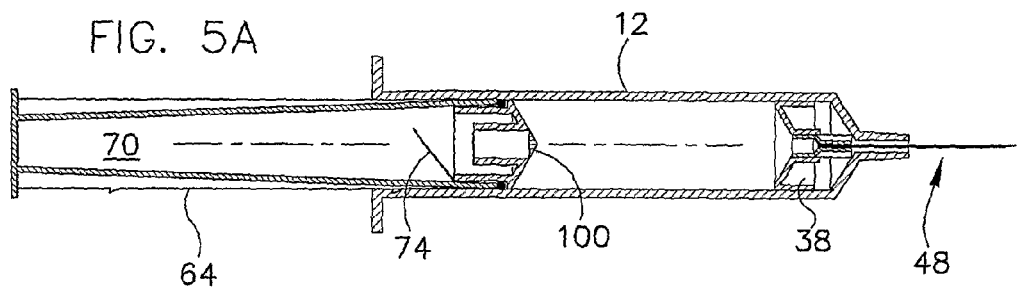
FIG. 5A is a side cross section of the syringe of FIG. 1 shown in an aspirated position.
Figure 5B:
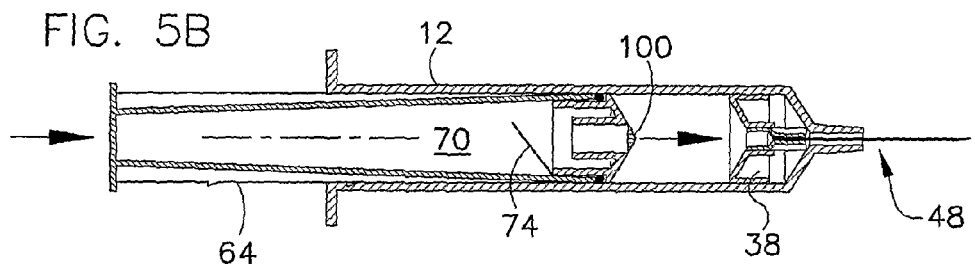
FIG. 5B is a side cross section of the syringe of FIG. 1 shown during an injection action.
Figure 5C:
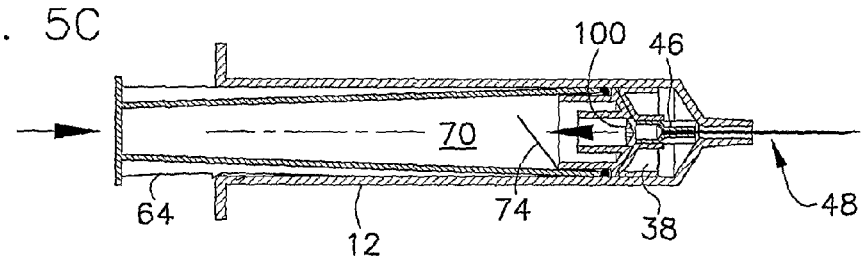
FIG. 5C is a side cross section of the syringe of FIG. 1 shown in a post-injection position.
Figure 5D:
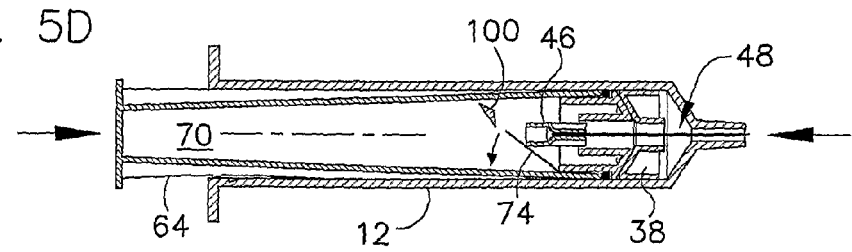
FIG. 5D is a side cross section of the syringe of FIG. 1 shown during needle retraction.
Figure 5E:
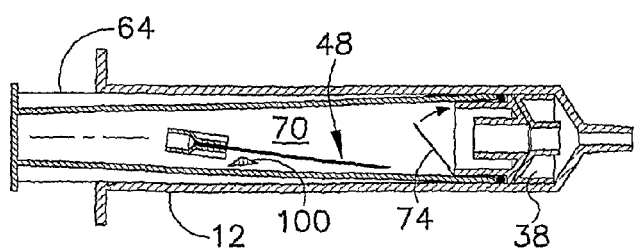
FIG. 5E is a side cross section of the syringe of FIG. 1 shown after needle retraction.

Further in the example in which the connecting elements include a piston connecting element 120 in the form of a projection on the piston subassembly 62 and a barrel connecting element 118 in the form of a notch, after the projection engages the notch, such as shown in FIG. 5E, the flat proximal end 119 of the notch will then keep the flat proximal end 121 of the projection from moving proximally, thereby keeping the piston from moving proximally with respect to the barrel.

Figure 6:
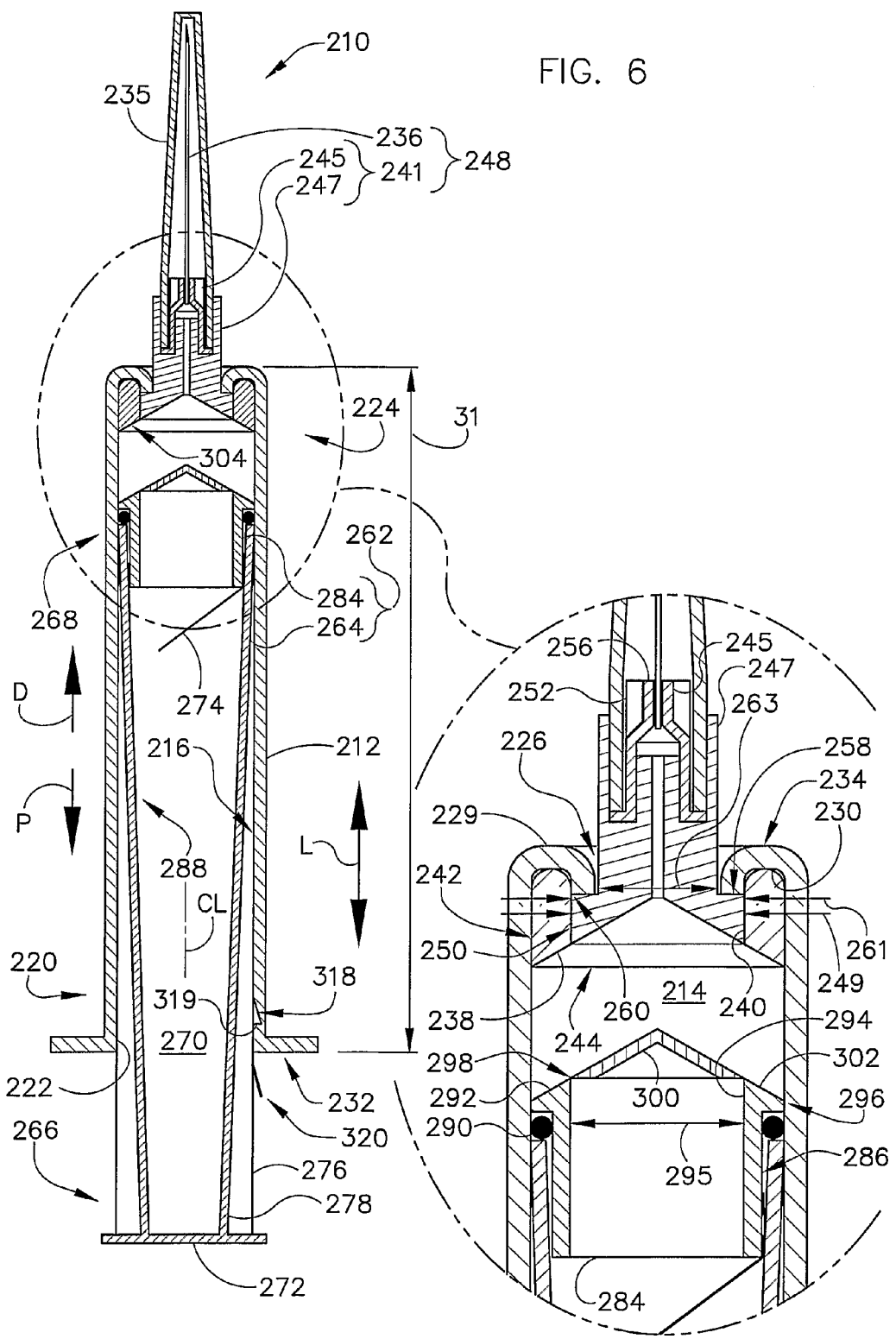
FIG. 6 is a side cross section of a syringe according to a second embodiment of the present invention.

To more easily pass beyond a male connecting element 118 or 120 or move into a female connecting element 118 or 120 of the barrel 12 or the piston 62, the mating element 118 or 120 may be a male connecting element including a flap or film of material, such as the flap 320 shown in FIG. 6 for engaging the barrel notch 318, which may include an end 319. As mentioned above, when one of the connecting elements, of the barrel 12 or of the piston 16, is a male element (e.g., projection), the other element, of the piston or the barrel, may be a female element. The mating elements 118, 120 may be positioned on the barrel 12 and piston 62 in other places instead of adjacent the proximal ends 20, 66, such as closer to the distal ends 24, 68 (e.g., adjacent the piston head 84). The connecting elements 118, 120 of the barrel 12 and the piston 62 are configured so that the connecting elements do not interfere with effective operation of the syringe 10 to aspirate and inject fluid and to retract the needle subassembly 48.

The part of the piston subassembly 62 becoming disposed in such groove of the barrel may include, for example, the piston body 64, the sealing element 90, and/or the periphery 96 of the piston head 84 (again, the periphery 96 of the piston head 84 may include the sealing element 90). As another example of the part of the subassembly 62 becoming disposed in such groove, the piston head 84 or piston body 64 can include a component that is biased outwardly (e.g., radially outward), such as by a cantilever or biased flap having a knob or small flange. Such part becomes disposed in the groove of the barrel 12 when the piston subassembly 62 is moved sufficiently in the distal direction D. The syringe 10 may be configured so that it is extremely difficult and perhaps generally impossible for a user to pull the piston subassembly 62 proximally back out of the barrel 12 after it has been locked in the barrel during the needle retraction operation. For example, the part of the piston subassembly 62 becoming disposed in the groove can be shaped and sized to generally disallow the part to withdraw from the groove when the user pulls the piston subassembly proximally with respect to the barrel 12.

The parts of the syringe 10 described above may include a variety of materials without departing from the scope of the present invention. For example, all or select parts of the barrel 12, the needle subassembly holder 38, the safety cap 41, the needle hub 41, the piston body 64, and the piston head 84 may include at least one of a plastic or a rubber.

FIGS. 5A-5E show various positions of the syringe 10 during operation. FIGS. 5A-5C show positions or states of the syringe 10 during a pre-retraction operation and FIGS. 5D and 5E show positioned of the syringe during the retraction operation. FIG. 5A shows the syringe 10 in an aspirated, or pre-injection, position in which the piston subassembly 62 is spaced from the needle subassembly 48. The syringe 10 may be disposed in its aspirated position by a user holding the barrel 12 and sliding the piston subassembly 62 in the proximal direction P with respect to the barrel. As with conventional syringes, the syringe 10 will take in fluid such as air, blood, or medication (not shown in detail), positioned at a tip 122 of the needle while the syringe is being aspirated.

FIG. 5B shows the syringe 10 during an injection action in which the piston subassembly 62 is moving in the distal direction D with respect to the barrel 12. During the injection mode, the syringe 10 will expel fluid (e.g., air, blood, medication) that was drawn into the barrel compartment 14 between the piston subassembly 62 and the needle subassembly 48 before the injection action.

FIG. 5C shows the syringe 10 in an injected, or post-injection, position in which the head 84 of the piston subassembly 62 is positioned adjacent the needle subassembly 48 and holder 38. From the injected position, the syringe 10 may be moved toward the aspirated position shown in FIG. 5A by moving the piston subassembly 62 in the proximal direction P (opposite to the piston motion shown in FIG. 5B). As mentioned above, the syringe 10 being moved toward the aspirated position (i.e., being aspirated) will take in fluid disposed at the needle tip 122 into the barrel 12 through the needle 36. Alternatively, from the injected position shown in FIG. 5C, the syringe 10 may be manipulated to retract the needle subassembly 48 as described below regarding FIGS. 5D and 5E.

Before the needle subassembly 48 is retracted from its extended distal position, the syringe 10 may be used multiple times for expelling and/or taking in fluids. This ability for multiple intake/expel actions can be beneficial in many scenarios, such as when medications must be withdrawn from separate viles and added to a common container for mixing before withdrawing the mixture and injecting it into a patient. The ability to use the syringe 10 multiple times for intaking/expelling fluid is another benefit of the syringe according to the present invention as compared to conventional safety syringes in which only a single injection action is possible. For example, some safety syringes are configured such that a piston head lockingly engages a needle when the piston is first moved to the injected position. This locking engagement enables the user to pull the needle back into the barrel and away from its extended distal position, but also keeps the user from performing any further aspirations or injections after the first injection.

FIGS. 5C-5E show the syringe 10 before, during, and after the needle-retraction action, respectively. To commence the retraction action, which may also be referred to as actuation or activation, the user simply pushes the piston subassembly 62 further distally with respect to the barrel 12 from the fully injected position shown in FIG. 5C. As described above, the syringe 10 is configured so that applying force on the needle subassembly holder 38 in the distal direction D using the head 84 of the piston subassembly 62 causes the needle subassembly 48 to move in the distal direction D. For example, in one embodiment, the needle subassembly 48 moves distally with the holder 38, which moves distally in response to the distally directed force caused by the user pushing the piston head 84.

During this initial part of the retraction action, in some embodiments of the present invention, when the needle subassembly 48 is pushed distally beyond its initial position (shown in FIGS. 1 and 5A-5C), the needle hub 41 contacts the barrel 12. In these embodiments, the distal contact portion 58 of the hub 41 is pressed against the contact portion 60 of the barrel 12 causing the barrel, which has elastic characteristics, to receive kinetic energy from the hub by slightly bowing or bending from its default or initial shape. By transferring force to the barrel 12 and the barrel bowing, the barrel 12 stores the energy as potential energy to be released when the barrel reflects back to its initial shape. The barrel 12 may be configured to bow in various ways, by various amounts, and in various portions of the barrel. For example, the barrel may bow in the conical portion 29, and also in a distal portion of a side of the barrel leading distally up to the conical portion. The portions of the barrel 12 that bow during the retraction operation may be referred to as a "bow" because of their bowing characteristics contributing to needle retraction.

The bowing barrel 12 is momentarily held by the needle hub 41 from reflecting back to its initial shape while it is being bowed in response to the force the needle hub is providing to the barrel in the distal direction. However, when the increasing amount of potential energy being stored in the bowing barrel 12 reaches a sufficient or threshold amount to overcome the holding forces (e.g., friction) holding the needle hub 41 and the needle subassembly holder 38 together, then the needle hub is displaced or propelled proximally P with respect to the holder by the barrel 12 reflecting back to its initial shape. The syringe 10 may be configured such that various amounts of force applied proximally on the holder 38 using the piston subassembly 62 are sufficient to overcome the joining force between the holder and the needle hub 41. Generally, the syringe 10 is configured so that the amount of force necessary to overcome this joining force, thereby retracting the needle subassembly 48 is small enough to easily be within the strength of most all users (e.g., nurses and physicians), but large or significant enough to avoid unintended needle retractions, such as during use of the syringe for taking in and expelling fluid.

As described above, it is contemplated that the syringe 10 may be configured so that forces other than that from the barrel 12 contribute some or all of the force required to retract the needle subassembly 48. For example, it is contemplated that the needle subassembly holder 38 may be configured so that when the needle hub 41 is being pressed against the barrel 12, a potential energy builds up in the holder that is translated to kinetic energy contributing to propelling the needle subassembly 36 proximally P when the potential energy is sufficient to overcome the holding forces (e.g., friction) holding the needle hub and the needle subassembly holder together. The holding forces are overcome when the force from the holder 38, or the forces from the holder and the barrel 12, reach a sufficient or threshold value(s).

As also described above, it is contemplated that the needle hub 41 may be configured so that when it is being pressed against the barrel 12, as the piston subassembly 48 is moved distally D beyond the injected position shown in FIG. 5C, the needle hub stores potential energy in response to the piston pressing against the hub, such as by the hub temporarily contracting or otherwise changing shape. This energy stored in the needle hub 41 increases until the holding forces (e.g., friction) temporarily joining the needle hub and the needle subassembly holder 38 are overcome. When the holding forces are overcome, the connection between the holder 38 and the hub 41 can be said to have failed, by design. The holding forces are overcome when the force from the needle hub 41, or the forces from the hub and the barrel 12 and/or the holder 38, reach a sufficient or threshold value. As described above regarding the reverse friction taper lock or reverse taper holder 38R, the hub 41R and the holder 38R configured generally as shown in FIG. 2 can also promote propelling of the hub with respect to the holder, such as by decreasing the threshold energy (s) needed to dislodge the hub from the holder and/or by contributing to the energy working to overcome the forces holding the hub in place adjacent the holder.

When the holding forces joining the needle hub 41 and the needle subassembly holder 38 are overcome in one or a combination of the ways described in the preceding paragraphs, the needle subassembly 48 including the needle hub and the needle 36 is propelled proximally P with respect to the barrel 12 and the needle subassembly holder 38. As shown in FIG. 5D, the propelled needle subassembly 48 contacts a proximal surface of the releasable portion 100 of the head 84 causing at least some of the releasable portion to separate from the distal surface 92 of the piston head 84. Because the releasable portion 100 is separated from the distal surface 92, the needle subassembly can pass through the hatchway 94 of the piston head 84. The needle subassembly 48 may force the releasable portion 100 to swing aside or to separate from a balance of the piston head 84 before and/or while the needle subassembly is passing through the hatchway 94. The syringe 10 may be configured so that the releasable portion 100 falls and/or is forced into the inner region 70 of the piston body 64 during the retraction operation after it is separated from the balance of the piston head 84 due to the force of the retracting needle subassembly 48.

As described above regarding components of the piston subassembly 62, the syringe 10 may include a one-way valve 74. The valve 74 may include a flap of material biased toward a position in which the flap at least partially blocks a path between at least some of the inner region 70 of the piston body 64 and the hatchway 94. The valve 74 bends (shown by arrow B in FIG. 5D) away from its default shape, position, or state when contacted by the needle subassembly 48 being propelled (shown by arrow P in FIG. 5D) proximally P. The needle subassembly 48 pushing through the one-way valve 74 in this way passes into the inner region 70 of the piston body 64. After the needle subassembly 48 passes the valve 74 and into the inner region 70 of the piston body 64, the valve moves to blocking shape, position, or state such as by returning to or near to its biased shape, position, or state, for blocking the needle subassembly from the hatchway 94.

For embodiments of the syringe 10 in which the piston body 64 includes the piston end cap 72, the needle subassembly 48 will be trapped in the inner region 70 of the piston body by the inner surface 88 of the piston body, including an inner surface of the end cap 72, and the piston valve 74. As described above, an embodiment (not shown) of the present invention is contemplated in which the piston body 64 does not include an end cap 72. In this embodiment, the needle subassembly 48 may be allowed to pass out of the piston body 64, such as into a separate disposal or recycling container for needles.

Whether the retracted needle subassembly 48 is retained in or passed through the piston body 64, such as into a special storage or stored in the piston body for storage, the needle is withdrawn from its dangerous extended distal position, thereby avoiding injury from skin puncture and virus transmission. In many cases, the embodiments of the present invention in which the piston body 64 includes a cap 72 are preferred because the needle subassembly 48 can easily be retracted into and stored safely in the piston body after the needle is used as desired for expelling and/or taking in fluids. The syringe 10 may be said to be in a safety state or stage after the needle subassembly 48 has been retracted into the piston body 64. According to at least one embodiment of the present invention, storing the needle in the inner region in this way prevents the needle from being easily removed without destroying the plunger body, after using the syringe.

FIG. 6 shows a syringe 210 according to a second embodiment of the present invention. The syringe 210 according to this embodiment shares many features including some common operating characteristics with the syringe 10 according to the first embodiment. For example, needle subassemblies of both syringes 10, 210 can be retracted by applying proximal force on a piston causing energy to be stored in the barrel, in a needle holder, and/or in a needle hub until that potential energy reaches a threshold amount sufficient to overcome forces joining the needle subassembly and the holder. Once the holding forces are overcome, the needle subassembly is propelled past a releasable portion of the piston subassembly, past a one-way valve, and into an inner region of the piston body. Primary differences between the syringes 10, 210 according to the first and second embodiments include variations in structure and corresponding variations in function, which are described more below.

The syringe 210 according the second embodiment includes a barrel 212 having an inner compartment 214 surrounded by an inner surface 216 and an outer surface 218 opposite the inner surface. The barrel 212 extends from a proximal end 220 including a proximal opening 222 to a distal end 224 including a distal opening 226. The distal opening 226 includes an engaging width 227, which, as with the other syringe 10 embodiment, is a width that a needle hub holding the needle must be at least as large as so that the needle hub may press against the barrel distal end 224 adjacent to the distal opening 226 for storing energy necessary to propel the needle subassembly proximally with respect to the barrel during needle retraction.

The barrel 212 may also include one or more handling flanges 228 extending from the outer surface 214 of the barrel. The barrel 212 may have various shapes and sizes without departing from the scope of the present invention. For example, as shown in FIG. 6, the distal end 224 of the barrel 212 may include a curved or otherwise bent portion 229 forming a distal barrel concavity 230. The curved portion may be part of what is referred to as the bow of the barrel 212, because it is configured to bend or bow during retraction of the needle subassembly 248. The bow may also include other portions of the barrel 212, such as portions of the side of the barrel 212 leading distally up to the curved portion.

The syringe 210 further includes a needle subassembly holder 238 positionable within the compartment 214 of the barrel 212. The holder 238 may also be referred to as a friction taper lock fitting because the fitting may be slightly tapered (e.g., having an inner diameter decreasing in the distal direction D). The holder 238 holds a needle 238 of the syringe 210 when the syringe is in an initial state (FIG. 6) in which the syringe may be used to take in and expel fluid. The holder 238 includes a body 239 forming a cavity 240 and, as with the syringe 10 according to the other embodiments, may have various shapes and sizes without departing from the scope of the present invention. The syringe 210 may also include a safety cap 235 for covering the needle 238 when the syringe is not being used to extract or inject fluid. As described above, the syringe 210 may be configured in a variety of ways for allowing the cap 235 to releasable connect to the balance of the syringe. As shown in FIG. 6, the cap 235 may releasably connect directly to the hub 241.

The needle subassembly holder 238 may be sized and shaped in a variety of ways, and include a variety of materials, without departing from the scope of the present invention. For example, the holder 238 may include an outer surface 242 that is sized and shaped to snugly engage the inner surface 216 of the barrel 212. In this and other embodiments, the holder 238 may be slidably received by and connected to the barrel 212 allowing the holder 238 to slide with respect to the barrel when a sufficient or threshold force for overcoming a strength of the connection between the holder and the barrel is applied to the holder. For example, for embodiments in which the holder 238 is only connected to the barrel 212 by a friction fit between the outer surface 242 of the holder and the inner surface 216 of the barrel, a sufficient force applied to a proximal end 244 of the holder in a distal direction D of the syringe 210 will overcome the friction force connecting the holder and barrel thereby causing the holder to move distally with respect to the barrel. The relative motion allowed between the holder 238 and the barrel 212 can also allow relative motion between a needle base or hub 241 holding the needle 238 and at least some of the barrel.

The needle hub 241 and the needle 238 may be referred to as a needle subassembly 248. The needle hub 241 is releasably connected to the needle subassembly holder 238. In one embodiment, the needle hub 241 is positioned within the cavity 240 of the holder 238. As shown in FIG. 6, the needle hub 241 of this embodiment includes a primary support 245 directly connected to the needle and a secondary support 247 directly connected to the primary support.

The primary and secondary supports 245, 247 may be connected in a variety of ways. For example, the primary and secondary supports 245, 247 may be connected by a conventional luer fit, such as a luer lock fit or a luer slip fit, or by other connections in which the supports 245, 247 have mating features, such as female portions (e.g., receptacles or hollow portions) of the primary/secondary support 245/247 for receiving mating male portions (e.g., protruding parts or protrusions) of the secondary/primary support 247/245. The connection between the primary and secondary supports 245, 247 may be configured to hold during syringe 210 operation so that the two supports 245, 247 move together as part of the needle subassembly 248. FIG. 6 shows a luer lock connection in which the primary support 245 is a male luer lock fitting and the secondary support 247 is a female luer lock fitting. One or both of the primary support 245 and secondary support 247 may include tapering so that the two are joined together in part due to tapered friction locking, such as by friction tapered luer lock fitting when the supports are configured to form a luer lock fit.

The needle hub 241 has a maximum width 249 and may include an outer surface 250 and one or more flanges 252 extending from the outer surface. For example, as shown in FIG. 6, the needle hub 241 may include multiple flanges 252 extending longitudinally (i.e., proximally and distally) along the outer surface 250 of the hub on the primary support 245. In one contemplated embodiment (not shown), the needle hub 241 includes flanges 252 on the secondary support 247. For example, a distal contact portion 258 of the secondary support 247 contacting a proximally-facing contact portion 260 of the barrel 212 may include flanges extending outward (e.g., radially outward) from a balance of the secondary support 247 for contacting the proximal contact portion of the barrel. For embodiments of the syringe 210 in which the needle hub 241 includes flanges 252, the maximum width 249 of the needle hub may be measured between lateral tips 254 of opposing flanges 252, such as the flanges (not shown) on the secondary support.

When the needle hub 241 is positioned in the holder 238, which is slidably positioned within the barrel 212, the hub, with the needle 238, may be slid with the holder in the distal direction D of the syringe 210 until the contact portion 258 of the hub contacts the contact portion 260 of the barrel. As described above, the barrel 212 includes a distal opening 226. The needle 238 extends through this opening when the needle subassembly 248 is initially positioned in the barrel 212 for use. As shown in FIG. 6, some of the needle hub 241 may also extend through the distal opening 226 of the barrel 212.

For embodiments in which the needle hub 241 and the needle 238 slide with respect to the barrel 212, the hub and the barrel should be sized and shaped so that the hub cannot slide through the opening and out of the barrel when the hub is pushed in the distal direction D. For example, the hub distal contact portion 258 has a width 261 being at least equal to a width 263 of the corresponding contact portion 260 of the barrel 12 for, at least in part, ensuring that the contact portion 258 of the hub 241 engages the contact portion 260 of the barrel when the needle subassembly holder 238, the needle hub 241, and the needle 238 are slid in the distal direction D within the barrel.

The width 263 of the hub contact portion 258 may correspond to (e.g., be equal to) the maximum width 249 of the needle hub 241. Contact between the needle hub 241 and the barrel 212 may keep the needle hub from exiting the barrel and may allow the barrel to receive and store energy from the hub (e.g., by bowing in response to distal force exerted on the barrel by the hub) and then release that energy (e.g., reflect back to an original barrel shape) thereby providing proximally directed P force on the needle thereby propelling the needle in the proximal direction. More about form of the barrel 212 related to this function and more about this function are described detail below.

The syringe 210 further includes a piston subassembly 262 having a piston body 264 slidably received within the barrel 212 such as by way of the proximal opening 222 of the barrel. The piston body 264 extends between a proximal end 266 and a distal end 268 and defines an inner region 270. The piston body 264 may include a cap 272, such as an end cap or wall positioned adjacent the distal end 268 of the body. Further, the piston body 264 may include a one-way valve 274 allowing the needle subassembly 248 to pass in the proximal direction P into the inner region 270 of the piston body 64 and impede the needle subassembly from passing in the distal direction D back out of the inner region of the piston body.

The piston subassembly 262 also includes a piston head 284 connected to the piston body 264 adjacent the distal end 268 of the piston body. The piston head 284 includes a distal surface 292 defining a central hole or hatchway 294. The hatchway 294 may have various shapes and sizes without departing from the scope of the present invention. For example, in one embodiment the hatchway 294 of this embodiment has a width 295 of between about 5 mm and about 12 mm, such as being between about 7 mm and about 10 mm. When the hatchway 294 is generally circular, the width 295 of the hatchway is a diameter. The width 295 of the hatchway 294 is equal to or greater than the maximum width 249 of the needle hub 241 so that the needle hub may pass through the hatchway, as described in further detail below.

The piston head 84 also includes a releasable portion 300 connected to the edge 298 of the hatchway 294 so that the releasable portion sealingly covers the entire hatchway. Thus, the piston head 284, including the sealing element 290, the distal surface 292, and the releasable portion 300 are slidable within the barrel 212 and create a seal disallowing any fluid disposed in the barrel 212 distal of the piston head from passing proximally beyond the piston head.

The distal surface 292 of the piston head 284 or a portion of that surface form a distal contact area 302 and the needle subassembly holder 238 includes a corresponding or mating proximal contact area 304. When the piston subassembly 262 is positioned in the barrel 212 such as shown in FIG. 6, the piston subassembly 262 is slidable within the barrel so that at least some of the piston distal contact area 302 generally aligns with and contacts at least some of the proximal contact area 304 of the holder 238 when the piston subassembly is moved distally to the holder 238.

The piston distal contact area 302 and the holder proximal contact area 304 may have various shapes and sizes without departing from the scope of the present invention. For example, the distal contact area 302 of the piston head 284 may be generally convex, sloping from a periphery 296 of the head distally and toward a centerline CL of the syringe 210 to the edge 298 of the hatchway 294, and the proximal contact area 304 of the holder 238 being generally concave, sloping from a periphery 306 of the holder distally and toward the centerline. The contact areas 302, 304 may be shaped and sized to ensure robust contact between the piston head 284 and the holder 238 so the piston subassembly 262 can push the holder effectively.

As with the syringe 10 according to other embodiments, it is contemplated that the holder 238 of the syringe 210 of the second embodiment may be configured so that energy can be built up in the holder and released to retract the needle subassembly during operation of the syringe 210. And, as also described above, the piston subassembly 262 may include a one-way or check valve 274 adjacent and proximal of the piston head 284. The valve 274 may be configured to allow the needle subassembly 248 passing through the hatchway 294 in the proximal direction P to pass into the inner region 270 of the piston body 264 and disallow the needle subassembly from passing in the distal direction D back out of the inner region of the piston body (i.e., back through the hatchway). Various types, sizes, and shapes of valves 274 may be used without departing from the scope of the present invention including exemplary valves described above regarding the syringe 10 embodiment exemplified in FIG. 1. Also, again, the valve 274 may be connected to the piston head 284 and piston body 264 in a variety of ways, such as being directly connected to the head and/or body or indirectly connected to one or both of the head and body.

Operation of the syringe 210 according to the second embodiment is similar to operation of the syringe 10 according to the first embodiment. For example, the syringe 210 may be moved between an aspirated position, analogous to that shown in FIG. 5A for the syringe 10 of the first embodiment, and an injected position, analogous to that shown in FIG. 5C, for expelling and/or taking in fluid.

Figure 7:
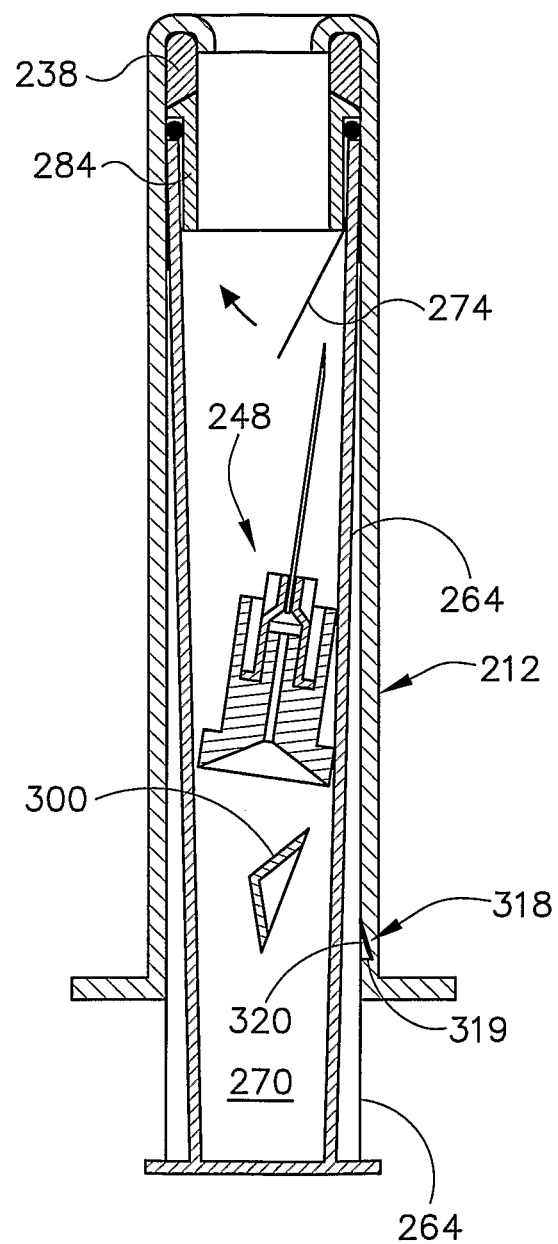
FIG. 7 is a side cross section of the syringe of FIG. 6 shown during needle retraction.

FIG. 7 shows the needle subassembly 248 retracting (i.e., being propelled away from the extended distal position shown in FIG. 6). To commence retraction, the user simply pushes the piston subassembly 262 further distally with respect to the barrel 212 from the fully injected position (analogous to the position shown in FIG. 5C regarding other syringe 10 embodiments). As described above regarding this and other embodiments, the syringe 210 is configured so that applying force on the needle subassembly holder 238 in the distal direction D using the head 284 of the piston subassembly 262 causes the needle subassembly 248 to move in the distal direction D.

During this initial part of the retraction action in some embodiments of the present invention, when the needle subassembly 248 is pushed distally beyond its initial position (shown in FIG. 6), the needle hub 241 contacts the barrel 212. Specifically, the distal contact portion 258 of the hub 241 is pressed against the contact portion 260 of the barrel 212 causing the barrel to receive kinetic energy from the hub by slightly bowing or bending from its default or initial shape. By bowing, the barrel 212 stores the energy as potential energy to be released when the barrel reflects back to its initial shape.

The bowing barrel 212 is momentarily held by the needle hub 241 from reflecting back to its initial shape while it is being bowed in response to the force the needle hub is providing to the barrel in the distal direction. However, when the increasing amount of potential energy being stored in the bowing barrel 212 reaches a sufficient or threshold amount to overcome the holding forces (e.g., friction) holding the needle hub 241 and the needle subassembly holder 238 together, then the needle hub is propelled proximally P with respect to the holder by the barrel 212 reflecting back to its initial shape.

As described above, it is contemplated that the syringe 210 may be configured so that forces other than that from the barrel 212 contribute some or all of the force required to retract the needle subassembly 248. For example, it is contemplated that the needle subassembly holder 238 may be configured so that when the needle hub 241 is being pressed against the barrel 212, a potential energy builds up in the holder that is translated to kinetic energy contributing to propelling the needle subassembly 236 proximally P when the potential energy is sufficient to overcome holding forces (e.g., friction) holding the needle hub and the needle subassembly holder together. The holding forces are overcome when the force from the holder 238, or the forces from the holder and the barrel 212, reach a sufficient or threshold value(s).

As also described above, it is contemplated that the needle hub 241 may be configured so that when it is being pressed against the barrel 212, as the piston subassembly 248 is moved distally D beyond the injected position, the needle hub stores potential energy in response to the piston pressing on the hub, such as by the hub temporarily contracting or otherwise changing shape. This energy stored in the needle hub 241 increases until the holding forces (e.g., friction) temporarily joining the needle hub and the needle subassembly holder 238 are overcome. The holding forces will be overcome when the force from the needle hub 241, or the forces from the hub and the barrel 212 and/or the holder 238, reach a sufficient or threshold value.

When the holding forces joining the needle hub 241 and the needle subassembly holder 238 are overcome in one or a combination of the ways described in the preceding paragraphs, the needle subassembly 248 including the needle hub and the needle 238 is propelled proximally P with respect to the barrel 212 and the needle subassembly holder 238. As shown in FIG. 7, the propelled needle subassembly 248 contacts a proximal surface of the releasable portion 300 of the head 284 causing at least some of the releasable portion to separate from the distal surface 292 of the piston head 284. Because the releasable portion 300 is separated from the distal surface 292, the needle subassembly can pass through the hatchway 294 of the piston head 284. The needle subassembly 248 may force the releasable portion 300 to swing aside or to separate from a balance of the piston head 284 before and/or while the needle subassembly is passing through the hatchway 294.

As described above regarding components of the piston subassembly 262, the syringe 10 may include a one-way valve 274. The needle subassembly 248 pushing through the one-way valve 274 also passes into the inner region 270 of the piston body 264. After the needle subassembly 248 passes the valve 274 and into the inner region 270 of the piston body 264, the valve moves to a blocking position such as by returning to or near to its biased shape, for blocking the needle from the hatchway 294.

The syringe 210 according to the second embodiment may otherwise be identical to the syringe 10 according to the syringe 10 according to the first embodiment and, accordingly, is not described in further detail.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended listing of inventive concepts. Although specific terms are employed herein, they are used in a generic and descriptive sense only and not for purposes of limitation.

The invention claimed is:

1. A retractable-needle syringe assembly capable of a needle retraction operation, said assembly comprising:
    a hollow barrel extending from an open proximal end to a distal end, said distal end defining a needle opening therein, said barrel further having an inner surface including a proximally-facing contact portion, a flexible portion of said distal end of the barrel being capable of bowing under force and storing potential energy for later use in said needle retraction operation;
    a needle subassembly holder positioned at least partially in said barrel adjacent said inner surface of said barrel;
    a needle subassembly including:
        a needle hub releasably connected to said needle subassembly holder by holding forces, said needle hub having a maximum width and a distal end configured to engage said proximally-facing contact portion of the barrel; and
        a needle connected to said needle hub and extending through said needle opening during the pre-retraction use of the syringe; and
    a piston subassembly slidably disposable within said barrel through the open proximal end of the barrel, said piston subassembly including:
        a piston body extending from a proximal end to a distal end and defining an inner region for receiving said needle subassembly during a retraction operation of said syringe assembly; and
        a piston head positioned at or adjacent said distal end of said piston body, said head extending from a periphery to an edge of an inner hatchway and said head also having a releasable portion temporarily covering an entirety of said hatchway and releasably connected to said edge of said hatchway, said hatchway having a width greater than said maximum width of said needle hub and said periphery of the head being configured to form a seal with said inner surface of the barrel when said piston subassembly is positioned within said barrel;
    wherein said flexible portion is configured to bend from an initial shape and thereby store potential energy as the needle hub is pressed against the proximally-facing contact portion of the barrel of the syringe assembly; and
    wherein said retractable-needle syringe assembly is configured to develop and release a level of potential energy during said needle retraction operation of the syringe assembly, during which said flexible portion is configured to bend until the potential energy stored in said barrel and any other parts of said needle syringe assembly combine to reach said developed amount of potential energy, and forces on said needle hub reach a threshold value sufficient to release said needle hub from said holder and such that said level of potential energy developed during said needle retraction operation of said syringe assembly is sufficient upon its release to propel said needle subassembly in a proximal direction through said hatchway and into said piston body, thus completing said needle retraction operation.

2. A retractable-needle syringe assembly as set forth in claim 1 wherein said needle subassembly holder includes a cavity and said needle hub is releasably connected to the holder in said cavity.

3. A retractable-needle syringe assembly as set forth in claim 2 wherein said needle subassembly holder and said needle hub are shaped so that said holder matingly receives said needle hub in said cavity of the needle subassembly holder.

4. A retractable-needle syringe assembly as set forth in claim 3 wherein:
    said needle subassembly holder has at least one inner wall defining the cavity;
    said cavity has a cavity width measured between opposing points on the inner wall;
    said holder inner wall tapers so that the cavity width increases from a minimum at a distal end of the cavity to a maximum at a proximal end of the cavity;
    said hub having an outer wall and a hub width measured between opposing points on the hub outer wall; and
    said hub outer wall tapers so that the hub width increases from a minimum hub width at a distal end of the hub to said maximum width at a proximal end of the hub.

5. A retractable-needle syringe assembly as set forth in claim 1 wherein said needle subassembly holder includes a proximal contact area and said piston head includes a distal contact area generally aligned with said proximal contact area of the needle subassembly holder so that at least some of said distal contact area of the head can press against at least some of the proximal contact area of said needle subassembly holder when said piston subassembly is pushed in a distal direction, leaving a base of the needle unobstructed.

6. A retractable-needle syringe assembly as set forth in claim 5 wherein said piston subassembly includes a reinforcing flange extending in a proximal direction from the edge of said hatchway.

7. A retractable-needle syringe assembly as set forth in claim 1 wherein said body of the piston subassembly has an end wall spaced proximally from said piston head for keeping said needle subassembly from passing out of said inner region of the body in a proximal direction when said inner portion receives the needle subassembly during operation of the syringe assembly.

8. A retractable-needle syringe assembly as set forth in claim 5 wherein said piston subassembly further includes a one-way valve positioned proximally of the hatchway and configured to allow said needle subassembly to pass though said hatchway in the proximal direction and into said inner region but keep the needle subassembly from then passing back through the hatchway in a distal direction.

9. A retractable-needle syringe assembly as set forth in claim 8 wherein said valve includes a flap, which said needle subassembly moves as it passes in the proximal direction through said hatchway and into said inner region and which keeps said needle subassembly from passing back through the hatchway.

10. A retractable-needle syringe assembly as set forth in claim 1 wherein said needle hub includes a primary support directly connected to said needle.

11. A retractable-needle syringe assembly as set forth in claim 10 wherein said needle hub further includes a secondary support indirectly connected to said needle by way of the primary support to which said secondary support is directly connected, and wherein said needle and said needle hub pass together through said hatchway and into said inner region of the piston subassembly during a retraction operation of said syringe assembly.

12. A retractable-needle syringe assembly as set forth in claim 11 wherein said primary support includes a hollow portion and said secondary support includes a mating portion positioned within said hollow portion of the primary support.

13. A retractable-needle syringe assembly as set forth in claim 11 wherein the secondary support includes a hollow portion and the primary support includes a mating portion positioned within the hollow portion of the secondary support.

14. A retractable-needle syringe assembly as set forth in claim 11 wherein said primary support and said secondary support are configured to connect by at least a luer connection.

15. A retractable-needle syringe assembly as set forth in claim 1 wherein said needle subassembly holder is slidably received within the barrel.

16. A retractable-needle syringe assembly as set forth in claim 1 wherein said inner surface of the barrel includes a barrel connecting element, said piston subassembly includes a piston connecting element, and said barrel and piston subassembly are configured so that said connecting elements engage each other during said needle-retraction operation thereby locking the piston subassembly from moving proximally in the barrel.

17. A retractable-needle syringe assembly as set forth in claim 16 wherein said piston connecting element includes a projection of said piston body.

18. A method of using a safety syringe assembly having: a) a hollow barrel including a proximally facing contact portion; b) a needle subassembly holder slidably disposed within said barrel; c) a needle subassembly positioned at least partially in said barrel, said needle subassembly releasably connected to said holder by holding forces, and said needle subassembly including a needle hub connected to a needle; d) a piston subassembly slidably disposed within said barrel and having a hollow piston body and a piston head positioned adjacent a distal end of said body, said head extending from a periphery to an edge of a hatchway and having a releasable portion temporarily covering said hatchway and releasably connected to said edge; wherein the needle subassembly is positioned for pre-retraction use so that said needle extends through a distal opening of said barrel, the method comprising:
  retracting the needle subassembly by moving it from a pre-retraction position to a retracted position such that a predetermined level of potential energy is accumulated and then released during movement between said two positions, said retracting done by pushing said piston subassembly distally within said barrel so as to apply, using the piston head, a distal force on the holder sufficient to move the holder distally, thereby causing said needle hub held by said holder to press against the proximally facing contact portion of said barrel causing the barrel to bow from an initial pre-retraction shape to store at least a portion of said predetermined level of potential energy until said stored potential energy reaches said predetermined level of potential energy and until forces having a threshold value sufficient to cause said barrel to rebound toward the initial shape are reached, such that the predetermined level of potential energy is sufficient upon release to push said needle subassembly proximally to a safety position within said piston body, said safety position being said retracted position, thus completing said retracting.

19. A method of using a safety syringe assembly according to claim 18 wherein:
  said piston subassembly further includes a valve positioned at least in part proximally of said hatchway;
  during said step of retracting the needle subassembly, said propelled needle subassembly contacts said releasable portion and dislocates at least some of said releasable portion from said edge of the hatchway; and
  during said step of retracting the needle subassembly, said propelled needle subassembly contacts and moves said valve of the piston subassembly from a blocking position to a passing position, therein passing proximally past said valve.

20. A method of using a safety syringe assembly according to claim 19 further comprising maintaining said needle subassembly in said piston body including providing said valve so that the valve automatically returns to said blocking after being moved to said passing position allowing said needle subassembly to pass, thereby blocking said needle subassembly from passing distally beyond said valve and out of said piston body.

21. A method of using a safety syringe assembly according to claim 18 further comprising:

prior to said retracting step, taking fluid into the syringe assembly by translating said piston subassembly proximally with respect to said barrel to receive fluid positioned adjacent a tip of the needle by way of the needle and into said barrel;

expelling said fluid by translating the piston subassembly distally with respect to said barrel to expel the received fluid by way of said needle; and repeating said steps of taking in and expelling fluid at least one time before said retracting step.

22. A method of using a safety syringe assembly according to claim 18 wherein said barrel includes a male or female connecting element, one of said piston head or said piston body includes a female or male connecting element corresponding to said connecting element of the barrel, and said method further comprises locking said piston assembly in a distal position within said barrel by moving the piston subassembly distally until said connecting element of said piston head or the piston body engages said connecting element of the barrel.

23. A safety syringe assembly configured to be moved from a first, pre-ejection, configuration to a second, ejection, configuration in which a retractable needle is moved to a retracted position, said syringe comprising:

A) a hollow barrel extending from an open proximal end to a distal end, and having a distal opening and also having a proximally facing contact portion;

B) a needle subassembly holder slidably disposed within said hollow barrel proximate said distal end of said hollow barrel;

C) a needle subassembly positioned at least partially in said barrel, said needle subassembly releasably connected to said needle subassembly holder by a holding force, said needle subassembly including a needle hub connected to a needle, said needle configured to extend through said distal opening of the barrel; and D) a piston subassembly slidably disposed within said barrel and having a hollow piston body and a piston head positioned adjacent a distal end of said body, said piston head extending from a periphery to an edge of a hatchway and having a releasable portion temporarily covering said hatchway and releasably connected to said edge;

wherein said various elements interact such that said piston subassembly may be pushed distally within said barrel from a first, pre-ejection, position to a second, ejection, position, with said pushing being capable of being done: 1) to a position such that needle hub held by said needle subassembly holder presses in a distal direction against said proximally facing contact portion of said barrel, causing said barrel to bow, and said proximally facing contact portion of said barrel correspondingly pushes back in a proximal direction, and develops potential energy due to said bowing; 2) with a force sufficient to cause an amount of developed potential energy to be built up within said safety syringe assembly, including but not limited to potential energy being built up due to said bowing of said barrel, said amount of developed potential energy in said safety syringe being developed between said first, pre-ejection, configuration and said second, ejection, configuration; and 3) until said piston assembly reaches said second, ejection, configuration such that said holding force between said needle subassembly and said needle subassembly holder is overcome, at least in part by said proximal force from said proximally facing contact portion of said barrel, and said needle subassembly and said needle subassembly holder separate, said barrel rebounds to its pre-ejection position, and wherein said developed amount of potential energy is sufficient to push said needle subassembly proximally through said hatchway to a safety position within said piston body, said safety position being said retracted position.

24. A method of using a safety syringe assembly having a retractable needle movable to a retracted position, said method comprising the steps of:

A) Providing said safety syringe assembly, said safety syringe assembly comprising:
1) a hollow barrel extending from an open proximal end to a distal end, and having a distal opening and also having a proximally facing contact portion;
2) a needle subassembly holder slidably disposed within said hollow barrel proximate said distal end of said hollow barrel;
3) a needle subassembly positioned at least partially in said barrel, said needle subassembly releasably connected to said needle subassembly holder by a holding force, said needle subassembly including a needle hub connected to a needle, said needle configured to extend through said distal opening of the barrel; and
4) a piston subassembly slidably disposed within said barrel and having a hollow piston body and a piston head positioned adjacent a distal end of said body, said piston head extending from a periphery to an edge of a hatchway and having a releasable portion temporarily covering said hatchway and releasably connected to said edge;

B) Configuring said safety syringe assembly in a first, pre-ejection, configuration having the relationships described in Step "A", and said needle extending through said distal opening of the barrel; and C) Pushing said piston subassembly distally within said barrel from said first, pre-ejection, configuration to a second, ejection, configuration, said pushing of said piston subassembly being done:
1) to a position such that needle hub held by said needle subassembly holder presses in a distal direction against said proximally facing contact portion of said barrel, causing said barrel to bow, and said proximally facing contact portion of said barrel correspondingly pushes back in a proximal direction, and develops potential energy due to said bowing;
2) with a force sufficient to cause an amount of developed potential energy to be built up within said safety syringe assembly, including but not limited to potential energy being built up due to said bowing of said barrel, said amount of developed potential energy in said safety syringe assembly being developed between said first, pre-ejection, configuration and said second, ejection, configuration; and
3) until said piston assembly reaches said second, ejection, position such that said holding force between said needle subassembly and said needle subassembly holder is overcome, at least in part by said proximal force from said proximally facing contact portion of said barrel, and said needle subassembly and said needle subassembly holder separate, said barrel rebounds to its pre-ejection position, and wherein said developed amount of potential energy is sufficient to push said needle subassembly proximally through said hatchway to a safety position within said piston body, said safety position being said retracted position.

\* \* \* \* \*